United States Patent
Ringeisen et al.

(10) Patent No.: US 9,579,416 B2
(45) Date of Patent: *Feb. 28, 2017

(54) HIGH DENSITY FIBROUS POLYMERS SUITABLE FOR IMPLANT

(71) Applicant: Kensey Nash BVF Technology, LLC, Wilmington, DE (US)

(72) Inventors: Timothy A. Ringeisen, Exton, PA (US); William Christopher Wattengel, West Chester, PA (US)

(73) Assignee: KENSEY NASH BVF TECHNOLOGY LLC, Wilmington, DE (US)

( * ) Notice: Subject to any disclaimer, the term of this patent is extended or adjusted under 35 U.S.C. 154(b) by 70 days.

This patent is subject to a terminal disclaimer.

(21) Appl. No.: 14/159,427

(22) Filed: Jan. 20, 2014

(65) Prior Publication Data

US 2014/0287014 A1    Sep. 25, 2014

Related U.S. Application Data

(60) Continuation of application No. 13/481,575, filed on May 25, 2012, now Pat. No. 8,633,299, which is a (Continued)

(51) Int. Cl.
| | |
|---|---|
| A61B 17/68 | (2006.01) |
| C08L 5/04 | (2006.01) |
| A61L 27/16 | (2006.01) |
| A61B 17/70 | (2006.01) |
| A61B 17/72 | (2006.01) |
| A61L 26/00 | (2006.01) |
| A61L 27/24 | (2006.01) |
| A61L 27/46 | (2006.01) |
| A61L 27/48 | (2006.01) |
| A61L 27/52 | (2006.01) |
| A61L 27/56 | (2006.01) |
| A61L 27/58 | (2006.01) |
| C08H 1/06 | (2006.01) |
| C08L 5/08 | (2006.01) |
| C08L 67/04 | (2006.01) |
| C08L 89/06 | (2006.01) |
| A61L 27/18 | (2006.01) |
| A61L 27/20 | (2006.01) |
| A61L 27/22 | (2006.01) |

(Continued)

(52) U.S. Cl.
CPC ........... *A61L 27/16* (2013.01); *A61B 17/68* (2013.01); *A61B 17/70* (2013.01); *A61B 17/72* (2013.01); *A61L 26/008* (2013.01); *A61L 26/0033* (2013.01); *A61L 27/18* (2013.01); *A61L 27/20* (2013.01); *A61L 27/225* (2013.01); *A61L 27/227* (2013.01); *A61L 27/24* (2013.01); *A61L 27/3616* (2013.01); *A61L 27/3804* (2013.01); *A61L 27/3834* (2013.01); *A61L 27/46* (2013.01); *A61L 27/48* (2013.01); *A61L 27/52* (2013.01); *A61L 27/56* (2013.01); *A61L 27/58* (2013.01); *C08H 1/06* (2013.01); *C08L 5/04* (2013.01); *C08L 5/08* (2013.01); *C08L 67/04* (2013.01); *C08L 89/06* (2013.01); *A61B 17/7062* (2013.01); *A61B 2017/00526* (2013.01); *A61F 2/3094* (2013.01); *A61F 2/4241* (2013.01); *A61F 2/4465* (2013.01); *A61F 2002/30062* (2013.01); *A61F 2002/4475* (2013.01); *A61F 2002/4495* (2013.01); *A61F 2210/0004* (2013.01); *A61F 2310/00365* (2013.01); *C08K 3/0033* (2013.01); *C08L 2205/16* (2013.01)

(58) Field of Classification Search
CPC ......... A61B 17/68; A61B 17/70; A61B 17/72; A61B 17/7062; A61B 2017/00526; A61L 26/0033; A61L 26/008; A61L 27/16; A61L 27/18; A61L 27/20; A61L 27/225; A61L 27/227; A61L 27/24; A61L 27/3616; A61L 27/3804; A61L 27/3834; A61L 27/46; A61L 27/48; A61L 27/52; C08H 1/06; C08L 5/04; C08L 5/08; C08L 67/04; C08L 89/06; A61F 2/3094; A61F 2/4241; A61F 2/4465; A61F 2002/30062; A61F 2002/4475; A61F 2002/4495; A61F 2210/0004; A61F 2310/00365

See application file for complete search history.

(56) References Cited

U.S. PATENT DOCUMENTS

| | | | | |
|---|---|---|---|---|
| 3,742,955 A | * | 7/1973 | Battista | ................ A61L 15/325 106/157.3 |
| 6,179,872 B1 | * | 1/2001 | Bell | ........................ A61L 27/24 428/304.4 |

* cited by examiner

*Primary Examiner* — Irina S Zemel
(74) *Attorney, Agent, or Firm* — Steven Link

(57) ABSTRACT

This invention includes malleable, biodegradable, fibrous compositions for application to a tissue site in order to promote or facilitate new tissue growth. One aspect of this invention is a fibrous component that provides unique mechanical and physical properties. The invention may be created by providing a vessel containing a slurry, said slurry comprising a plurality of natural or synthetic polymer fibers and at least one suspension fluid, wherein the polymer fibers are substantially evenly dispersed and randomly oriented throughout the volume of the suspension fluid; applying a force, e.g., centrifugal, to said vessel containing said slurry, whereupon said force serves to cause said polymer fibers to migrate through the suspension fluid and amass at a furthest extent of the vessel, forming a polymer material, with said polymer material comprising polymer fibers of sufficient length and sufficiently viscous, interlaced, or interlocked to retard dissociation of said polymer fibers.

30 Claims, 8 Drawing Sheets

Related U.S. Application Data continuation of application No. 13/027,025, filed on Feb. 14, 2011, now Pat. No. 8,188,229, which is a division of application No. 11/741,611, filed on Apr. 27, 2007, now Pat. No. 7,910,690, which is a continuation of application No. 11/178,175, filed on Jul. 8, 2005, now Pat. No. 7,214,765, which is a continuation of application No. PCT/US2004/019805, filed on Jun. 19, 2004, which is a continuation-in-part of application No. 10/601,216, filed on Jun. 20, 2003, now Pat. No. 6,974,862.

(51) Int. Cl.
*A61L 27/36* (2006.01)
*A61L 27/38* (2006.01)
*A61B 17/00* (2006.01)
*A61F 2/30* (2006.01)
*A61F 2/42* (2006.01)
*A61F 2/44* (2006.01)
*C08K 3/00* (2006.01)

HIGH DENSITY FIBROUS POLYMERS SUITABLE FOR IMPLANT

RELATED APPLICATION

This application is a Continuation of U.S. patent application Ser. No. 13/481,575, filed on May 25, 2012, now U.S. Pat. No. 8,633,299, entitled HIGH DENSITY FIBROUS POLYMERS SUITABLE FOR IMPLANT, which is a Continuation of U.S. patent application Ser. No. 13/027,025, filed on Feb. 14, 2011, now U.S. Pat. No. 8,188,229, entitled HIGH DENSITY FIBROUS POLYMERS SUITABLE FOR IMPLANT, which is a Divisional of U.S. patent application Ser. No. 11/741,611, filed on Apr. 27, 2007, now U.S. Pat. No. 7,910,690, entitled HIGH DENSITY FIBROUS POLYMERS SUITABLE FOR IMPLANT, which is a Continuation of U.S. patent application Ser. No. 11/178,175, filed on Jul. 8, 2005, now U.S. Pat. No. 7,214,765, entitled HIGH DENSITY FIBROUS POLYMERS SUITABLE FOR IMPLANT, which was a Continuation of PCT International Patent Application Ser. No. PCT/US04/19805, filed on Jun. 19, 2004, and designating the U.S., entitled High Density Fibrous Polymers Suitable for Implant, which was a Continuation-in-Part of U.S. patent application Ser. No. 10/601,216, filed on Jun. 20, 2003, now U.S. Pat. No. 6,974,862, entitled HIGH DENSITY FIBROUS POLYMERS SUITABLE FOR IMPLANT, all of which are assigned to the same assignee as this invention, and whose disclosure is incorporated by reference herein.

BACKGROUND OF THE INVENTION

The invention generally relates to medical devices and procedures. The invention more particularly concerns a polymeric construct having interlaced and interlocked fibers and products formed from the fibrous polymer.

To better treat our aging population, physicians are looking for new and better products and methods to enhance the body's own mechanism to produce rapid healing of musculoskeletal injuries and degenerative diseases. Treatment of these defects has traditionally relied upon the natural ability of these types of tissue to repair themselves. In many instances the body is unable to repair such defects in a reasonable time, if at all. Advances in biomaterials has allowed for the creation of devices to facilitate wound healing in both bone and soft tissues defects and injuries. Such devices are used in tissue regeneration as tissue (e.g., bone) graft scaffolds, for use in trauma and spinal applications, and for the delivery of drugs and growth factors.

Bone and soft tissue repair is necessary to treat a variety of medical (e.g., orthopedic) conditions. For example, when hard tissue such as bone is damaged as a result of disease or injury, it is often necessary to provide an implant or graft to augment the damaged bone during the healing process to prevent further damage and stimulate repair. Such implants may take many forms (e.g., plugs, putties, rods, dowels, wedges, screws, plates, etc.), which are placed into the tissue. Typically, such implants can be rigid, flexible, deformable, or flowable and can be prepared in a variety of shapes and sizes. For non-rigid structural repair materials (e.g., putties and pastes) to be conveniently used, they must be capable of being formed into a variety of complex shapes to fit the contours of the repair site. An accurately configured implant that substantially fills the defect site will enhance the integration of natural bone and tissue to provide better healing over time. The prior art discloses medical implants that comprise, at least partly, collagen (to be discussed later).

Collagen is the most abundant protein found in the body. The unique chemistry of collagen makes it an ideal polymer for structural and hemostatic applications in both clinical and diagnostic settings. Collagen, like all proteins, is comprised of amino acids linked covalently through peptide or amide linkages. The sequence of the amino acids, or the primary structure, outlines the three-dimensional structure of the protein, which in turn dictates the function, and properties of the molecule. Collagen is composed of three peptide chains associated in a triple helical orientation. These triple helices associate to form fibrils, which ultimately make up connective tissue and other structural members.

Collagen has been used in a number of applications in the art. For example, one application is for use in hemostatic devices for the stoppage of bleeding, such as is described in U.S. Pat. No. 5,310,407 (Casale) and U.S. Pat. No. 4,890,612 (Kensey). However, neither teaches the use of native insoluble fibrous collagen. In U.S. Pat. No. 5,425,769, Snyders, Jr. discloses a biocompatible and bioresorbable bone substitute with physical and chemical properties similar to bone, consisting of reconstituted fibrillar collagen within a calcium sulfate di-hydrate matrix. The ratios of calcium sulfate and collagen are adjusted for each application and the bone substitute is molded in situ to form a solid phase. Snyders Jr. discloses an implant that remains malleable only for a brief period, as the combination of fibrillar collagen and calcium sulfate di-hydrate matrix forms a hard composition. Furthermore, the collagen as described in the '769 patent is neither interlocked, nor interlaced, relying on the calcium sulfate to lend structural integrity.

The polymer utilized for the implant may be combined in application with a biologically active agent to enhance the tissue healing response or enhance the mechanical properties of the implant (e.g., U.S. Pat. No. 4,776,890 (Chu)). Chu discloses a process for creating matrix of collagen containing mineral particles, such that when wetted, the matrix is malleable and retains its integrity. The matrix as claimed by Chu incorporates up to 10% of the mass as collagen, and relies on the physical characteristic of the particles comprising the bulk of the matrix to lend the integrity, and upon exposure to fluids, would lead to dissociation of the material unless a cross-linking step is performed. However, this cross-linking process is disfavored by Chu, as it would discourage bone tissue ingrowth.

Huc et al. (U.S. Pat. No. 5,331,092) describes a process for preparing medical pads by grinding collagen, acidifying with acetic acid, homogenizing, molding and freeze-drying. The pad formed would readily fall apart upon exposure to aqueous fluids and thus requires cross-linking. The cross-linked pads hold together but have limited mechanical strength limiting their usefulness to hemostatic pads.

Nigam (U.S. Pat. No. 4,948,540) described a process for preparing a collagen dressing material by creating a slurry comprised of an acid solubilized collagen and a non-solubilized natively cross-linked collagen. The resultant slurry was molded, and freeze-dried into a pad. The pad did not have sufficient mechanical properties due to its excessive porosity and thus was compressed at a pressure of 15,000-30,000 psi and optionally cross-linked. To improve strength due to lack of fiber-to-fiber interaction, the device is compressed without interlacing of the individual fibers. The compression serves to compress in only one dimension, placing the fibers in close proximity in one orientation, rather than interlacing the fibers.

Li (U.S. Pat. No. 5,206,028) described a process for preparing a dense collagen membrane by first freeze-drying a collagen dispersion of random fibers to form a sponge. This sponge was then humidified, compressed and subjected to chemical cross-linking. The resultant sponge was strong, having randomly entangled masses of fibers going in all directions. This device as described by Li lacks interlacing of the insoluble collagen as the aqueous dispersion is lyophilized without first interlacing the insoluble components.

Li (U.S. Pat. No. 6,391,333) described a process wherein sheets of oriented biopolymeric fibers are formed into sheets by capturing them on a spinning mandrill that was rotated in a fibrous collagen slurry. The fibers were then compressed to force them closer together so they could be dried, preferably while in contact with a gluing agent. The sheet was then cut from the mandrill, inverted and cross-linked to form a sheet. Additional sheets could be individually stacked on top of each other to create thicker devices with greater mechanical strength. The device as constructed has fibers substantially aligned in parallel planes, and lacks equiaxial interlacing.

In PCT application WO 98/35653, Damien describes a process for preparing an implantable collagen putty material by acidifying a collagen solution to a pH of between 3.0 to 6.0. This produces a non-fibrous dough like material that can be used to suspend graft material. At higher pH, the collagen precipitates out, becoming crumbly with a consistency of wet sand.

It is well known to utilize a centrifuge or filtration press as a part of a rinsing procedure, or a 'wash step' to remove insoluble components contained within the solution. Nishihara (U.S. Pat. No. 3,034,852) describes a process to solubilize previously insoluble collagen fibers without denaturation of the protein structure by using hydrolytic enzymes. In the examples, the author describes separation of the fibers from the wash solution by centrifugation or filtration press methods, the fibers are then brought back into solution. Additionally, the fibers, which are separated using this method are reconstituted fibers which tend to be small in size.

Highberger, et. al. (U.S. Pat. No. 2,934,446 and U.S. Pat. No. 2,934,447) describe a method, as well as, the physical preparation of collagen fiber masses to form leather-like sheets from hide scraps unusable in the traditional leather making process. This psuedo-leather may support small colonies of cells but would be unsuitable for tissue ingrowth. The method of concentration used is a precipitation technique, which creates a fiber dispersion. This slurry/dispersion as described included random clumps of undispersed or entangled fibers. Highberger combines a unique fiber that coacts with a high dissolved solids content collagen solution to form well knit, or leather like sheet. In the '447 patent, Highberger further refines the process of the '446 patent by incorporating a kneading step, which works the dough material to make the product free from lumps, the kneading necessarily disrupts any interlacing or interlocking fibers prior to precipitating the solubilized collagen.

SUMMARY OF THE INVENTION

This invention includes malleable, biodegradable, fibrous compositions for application to a tissue site in order to promote or facilitate new tissue growth. One aspect of this invention is a fibrous component (e.g., collagen, chitosan, alginate, hyaluronic acid, poly-lactic acid, poly-caprolactone, and polyurethane) which provides unique mechanical and physical properties, as will be discussed.

Fibers may be suspended within a suspension fluid (preferably aqueous) forming a relatively homogenous slurry/dispersion. This dispersion preferably has a low solid content whereby the organizing process, e.g., centrifugation, causes the material to have preferable mechanical and physical properties.

The physical properties may include, but are not limited to, injectable, flexible, compression resistant, or elastic properties. Biologic properties may include, but are not limited to, conductive or inductive properties for hard and soft tissues. Additionally, in a preferred embodiment, additives (e.g., fibers, particulate, or gels) may be used to further tailor the material properties.

In a preferred embodiment, the degree of centrifugation is specified to dictate the physical properties of the resulting material; alternatively, or in combination, a rehydration step may be tailored to affect the physical properties of the material, as will be discussed. As an example, the properties of this material may be tailored such that exposure to rehydration liquids or bodily fluids (e.g., blood) will render the material to be self-supporting. That is, the material will not readily slump under its own weight, even though it is readily moldable by hand pressure. This can be particularly useful during a procedure where the entire wound site is not immediately secured or enclosed by hard tissue or other constraint. Additionally, the implantable embodiments may contain biologically active agents, which may aid osteoconductivity or osteoinductivity.

In a preferred method, the material may be created by providing a vessel containing a slurry, said slurry comprising a plurality of natural or synthetic polymer fibers and at least one suspension fluid, wherein the polymer fibers are substantially evenly dispersed and randomly oriented throughout the volume of the suspension fluid, or at least exhibiting no significant organization or preferred orientation; applying a force, e.g., centrifugal, to said vessel containing said slurry, whereupon said force serves to cause said polymer fibers to migrate through the suspension fluid and amass at a furthest extent of the vessel, generally at a wall or similar surface of the vessel, forming a polymer material, with said polymer material comprising polymer fibers of sufficient length and sufficiently viscous, interlaced, or interlocked to retard dissociation of said polymer fibers.

DETAILED DESCRIPTION OF THE INVENTION

This invention is a malleable, biodegradable, fibrous composition for application to a tissue site in order to promote new tissue growth. One aspect of this invention is a fibrous component (e.g., collagen, chitosan, alginate, hyaluronic acid, polylactic acid, poly-caprolactone, and poly-urethane, etc.) (see table 1) which provides unique mechanical and physical properties, as will be discussed.

Fibers (e.g., collagen, chitosan, alginate, and hyaluronic acid), may be obtained, for the example of type I collagen, from bovine hide, which have been processed in a manner known by those skilled in the art. As an example, the hides are stripped from the animal carcass and the corium (i.e., the intermediate layer of an animal hide between the grain and the flesh sides) is subsequently split from the rest of the hide. The corium is limed using a calcium hydroxide solution to remove extraneous organic material. The limed corium is then neutralized using an acid solution and the excess salt produced is serially rinsed (e.g., with water). The neutralized corium is then ground using a mill type apparatus to tear apart the corium into fibers. This process maintains the native cross-links within the collagen. (During the aging process of the live animal, intermolecular and interfibrillar bonds are naturally formed between collagen fragments. These naturally occurring bonds are what distinguish the fibers of collagen as natively cross-linked fibers as opposed to reconstituted fibers of collagen). The fibers are suspended within a suspension fluid (preferably aqueous) forming a relatively homogenous slurry/dispersion. This dispersion preferably has a solid content ranging from 0.25 to 10%, but most preferably in the range of 3 to 5% by weight.

The resultant slurry is concentrated by centrifugation; preferably, at temperatures below 60 degrees Celsius to avoid degradation of the collagen and subsequent gelatin formation. Speed and therefore force, as well as time can be varied to create the desired extent of fiber interlacing, as will be discussed later. The slurry can be spun under forces of about 500×g (times gravity) to forces as high as about 30,000×g and for times ranging from 10 seconds to 96 hours. Preferably, the suspension is spun at forces of 500×g to 10,000×g and times of 1 minute to 24 hours. Most preferably the suspension is spun at 3000×g for about 5 minutes. This creates, in a preferred embodiment, a paste or putty-like structure containing interlocked or interlaced collagen fibers, as will be discussed, that may be molded and dried by either evaporation to create a high density non-porous unit, or by lyophilization to maintain the three dimensional structure and porosity. An additional preferred embodiment comprises a material that is a flowable, yet dense, material, which may be injected or otherwise molded. This moldable embodiment may be cast into a mold, or in situ, as will be discussed.

Figure 1A:
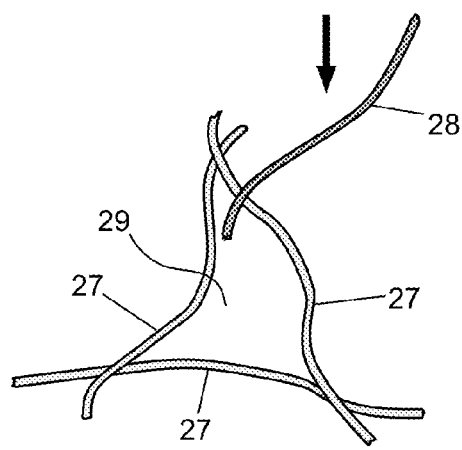
FIGS. 1A, B, and C are enlarged, representative diagrams depicting the arrangement of interlacing and interlocking fibers of the present invention, wherein a force (e.g., centrifugal) is applied in orientation represented by the arrow.
Figure 1B:
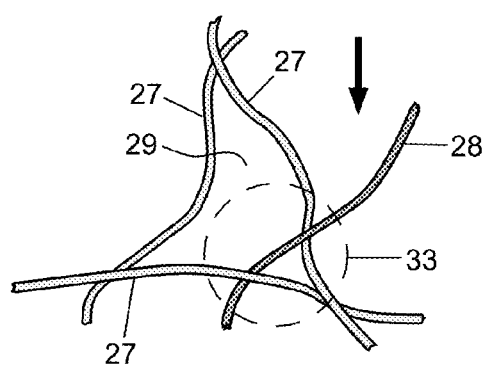

Referring to FIG. 1A, the interlacing phenomenon occurs as the fibers 27 and 28 migrate down through the suspension fluid, and the individual fibers interlace among other fibers, herein represented by interlacing fiber 28 becoming interlaced with other fibers 27, entering a region 29 bordered by other fibers 27. In FIG. 1A, it is desirable to start with a low solids content (e.g., below 10%) slurry so that the fibers are uniformly distributed and freely moving prior to centrifugation. Entangled clumps of fibers (not shown) may interfere with proper interlacing and should be minimized by starting with the low concentrations. Interlacing is a non-directional interlocking of fibers 27 randomly in three dimensions throughout the material, as opposed to layer-like or directional entanglement of the fibers, as will be discussed. FIG. 1B depicts interlacing 33 (represented by the zone within the dashed circle), as the low concentration fiber mix migrates and gradually intertwines itself during centrifugation, but does so in a three dimensional type of formation. Without wishing to be bound to any particular mechanism or explanation, it is believed that this phenomenon occurs because there is a nearly uniform load on all of the fibers 27, with the exaggerated gravitational load (i.e., from the centrifuge) tending to move the fiber 28, without necessarily rotating it. This, in turn, causes the fibers 27 and 28 to eventually coalesce and at least partially thread themselves together, to some degree as the interlacing fiber 28 enters the region 29 bordered by the other fibers 27.

As the interlacing 33 continues, the fibers come into contact with the surface of the container, in the centrifuge, or other fibers already compressed with the surface. As the fibers continue the migration, and eventually "pile up" or amass, they become further interlaced and eventually the fibers 28 may be deformed or bent as the pressure of other migrating fibers builds.

Figure 1C:
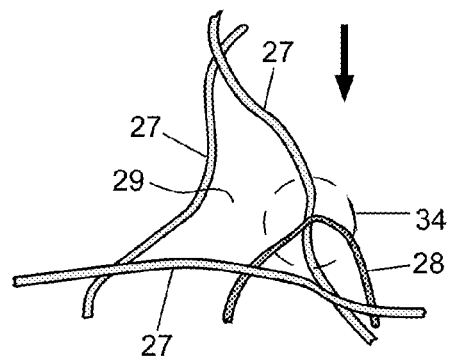

Referring to FIG. 1C, as the pressure builds, and the fibers 27 and 28 compress, the interlacing step is completed, and the deformation of the fibers causes them to interlock 34 (depicted by the dashed circle). It is this dual interaction of interlacing and interlocking that results in the unique properties of certain embodiments of the present invention.

In these various embodiments, the fibers are not externally pressed together (not shown), which causes the higher end of the fibers to be pressed downward (causing alignment) by the externally applied force (e.g., a platen). The non-uniform force ultimately causes a directional or anisotropic fiber bundle; similarly, the evaporation of the fluid from a preferential direction causes fiber bundling and alignment at the evaporating surface/interface.

Additionally, interlacing restricts the motion of fibers within a unit during rehydration, since all external surfaces are comprised of fibers which intrude into the material itself (not shown), thereby retarding disassociation of fibers from the unit upon contact with a fluid. Upon rehydration the dried structure forms a paste or putty-like material similar in characteristic to that of the pre-dried material, as will be discussed.

Likewise, interlacing of the fibers also provides greater multi-directional consistency (i.e., isotropy) in the mechanical properties as opposed to directional mingling of fibers. That is, the interlacing is three dimensional, and therefore provides uniform properties in the three dimensions; whereas the directional materials previously discussed yield materials with properties along the fiber axis (e.g., the plane of flattening or evaporation) that are very different from the properties perpendicular to the fiber axis.

Interlacing also provides biologic advantages over directional entanglement by providing an equiaxial structure (or a structural that more resembles an equiaxed structure's lack of directionality) for cellular infiltration as well as an advantageous platform for tissue formation. A structure that allows cells to infiltrate uniformly in all directions may improve overall tissue organization, and may also avoid, in soft tissue regeneration, the directional bundling common in fibrous scar tissue.

Centrifuging materials such as fibrous collagen will also create chemical linkages aside from physical interlacing that serve to reinforce the resulting matrix. In the particular case for collagen, the centrifugal force brings individual fibers and fibrils into close molecular proximity, and re-establishes non-covalent forces such as hydrogen bonding, hydrophobic/hydrophillic interactions, and electrostatic interactions, that these individual fibers and fibrils previously embodied in the native, pre-extracted tissue. These additional chemical linkages may act to create a pseudo-molecular weight increase to the matrix. Thus, the combinatorial effects of physical interlacing and chemical bonds impart unique cohesive properties and viscosity to these fibrous putties.

Although centrifugation is a preferred process, a similar interlacing may be accomplished by placing a low concentration slurry (e.g., less than 15% polymer) into a closed container and exposing it to a global force such as multi-axis gyroscopic mixing. This multi-axis mixing process causes flocculation of the fibers as they migrate through the suspension fluid towards the center of the closed container wherein they become interlaced with one another. The clumps of interlaced fibers that amass may then be exposed to a force that extracts a portion of the suspension fluid thereby allowing the fibers within the interlaced clumps to become interlocked with each other.

To improve the migration of fibers and prevent clumping during the interlacing process, as described above and expanded upon below, it is preferred to incorporate a percentage (e.g., 0%-50% by mass of fibers) of one or more lubricants (e.g., biocompatible oils, hydrogels, liquid polymers, low-molecular weight polymers, glycosaminoglycans, surfactants, waxes, fatty acids, fatty acid amines and metallic stearates such as zinc, calcium, magnesium, lead and lithium stearate, etc.) into the suspension fluid. A lubricant is defined as a substance, which is capable of making surfaces smooth or slippery. These characteristics are due to a reduction in friction between the polymer fibers to improve flow characteristics and enhance the knitting and wetting properties of the fibers. The lubricant may be liquid or solid and may be suspended or dissolved in a carrier solvent (e.g., water, alcohol, acetone, etc.). Additionally the lubricant may only become lubricious under shearing force or change in temperature. The lubricant may remain in its entirety in the final invention; may be partially removed in the dehydration/desolvation process; or, may be washed out or removed by methods known in the art during further processing. Lubricants that remain in the final invention may be biologically active agents or may form microstructures. Preferred lubricants include Tween-80, hyaluronic acid, alginate, glycerin or soluble collagen with the most preferred being acid soluble collagen such as Semed S produced by Kensey Nash Corporation (Exton, Pa.).

Additional ways in which to add lubricity include physically or chemically altering the surface of the fibers making up the composition. Such alterations can be achieved through chemical or physical attachment of a lubricious substance to the fibers, temperature induced phase changes to the surfaces of the fibers or partial solubilization of the fibers through alteration of the pH and/or conductivity of the free fluid or use of a percentage of solvent for the fibers within the free fluid. Other methods of creating lubricity are known to those skilled in the art, and are embraced by this disclosure.

During rehydration, the material absorbs liquid (e.g., water, bodily fluids, blood, etc.) to the limits of the void (i.e., pore) volume. Since a large portion of the surface fibers are intruding in the material, the inward ends are locked by mechanical and/or frictional means. This aspect of the interlacing phenomenon causes the material to remain intact while the fluid ingresses, with minimal fiber liberation to the non-absorbed liquid. In contrast, directionally pressed materials lose surface fiber during rehydration, since they are not anchored or interlocked (i.e., they lay parallel to the surface of the material).

In these various embodiments, the material will freely absorb liquid until the approximate pre-dried volume is attained; at which point the material is in a state of pseudo-equilibrium. This state is achieved because the interlocked fibers are re-hydrated, returning to their natural state (i.e., centrifuged position). The continued absorption of liquid will, over an extended period of time, cause the fibers to de-interlace (i.e., the working free of interlaced fibers). The action of partial de-interlacing, i.e., the movement of fibers against frictional and other mechanical locking within a region without total fiber separation, allows shifting or movement of zones that remain interlaced. Resistance to fiber movement within the interlaced zones, combined with the frictional forces of the de-interlaced regions gives the material the paste or putty-like consistency. In contrast, traditional collagen materials would rapidly dissociate into the re-hydrating fluid.

The continued exposure to liquids will cause the material to swell beyond the aforementioned pseudo-equilibrium, and impart some de-interlacing, however, this absorption occurs at a rate significantly less than the rate prior to achieving pseudo-equilibrium. This attribute in itself, may be useful, because certain embodiments of this invention may be sized for particular types of defects, and the near equilibrium state will be more easily achieved without careful monitoring of the rehydration level of the material.

Whether the optimum absorption level is achieved may be moot, because the size can be altered or molded by applying pressure (e.g., squeezing) to the material to cause the expulsion of some of the absorbed liquid. This feature is attractive, since it renders the material tailorable with regard to size, shape and consistency. Additionally, in a preferred embodiment, some or all of the liquid may be absorbed in vivo, thereby causing intimate contact along the entire defect cavity.

Figure 2:
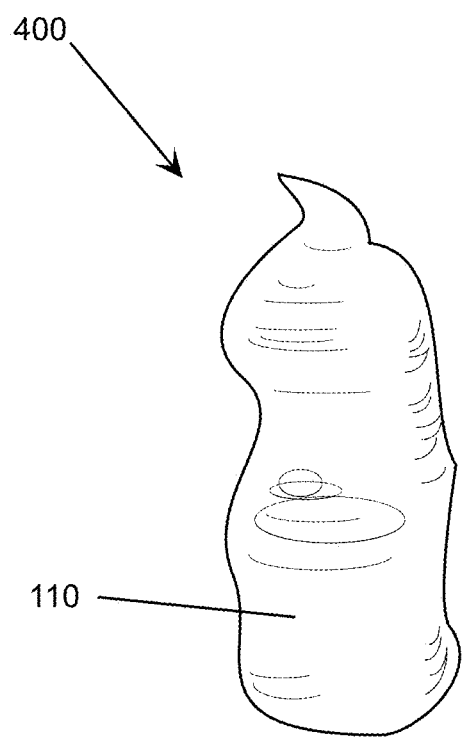
FIG. 2 depicts a hydrated malleable mass 400 of interlaced fibers 110.
Figure 3:
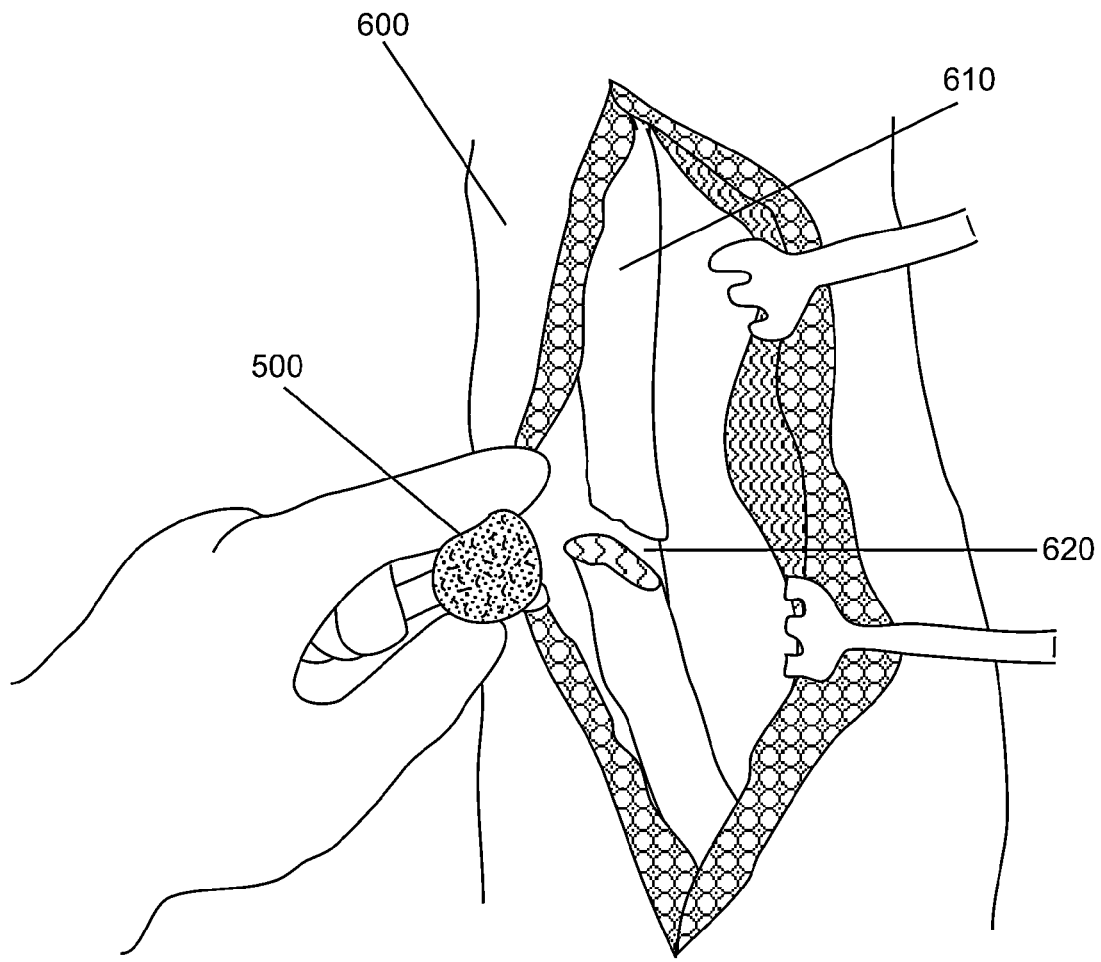
FIG. 3 depicts a human extremity 600 that has been surgically opened to reveal bone 610. A hydrated malleable mass 500 is being inserted into an exposed osseous defect 620.

As shown in FIG. 2, the consistency of the various embodiments of the invention allows them to form a malleable putty/paste 400 that can conform to unique shapes and contours encountered in tissue-engineering applications. The interlocking of the interlaced fibers 110 retards dissolution of the device, allowing it to be used in unconfined wounds (e.g., segmental defects as shown in FIG. 3). FIG.

3 depicts a human extremity 600 that has been surgically opened to reveal bone 610, a hydrated malleable mass 500 is being inserted into an exposed osseous segmental defect 620.

Figure 4:
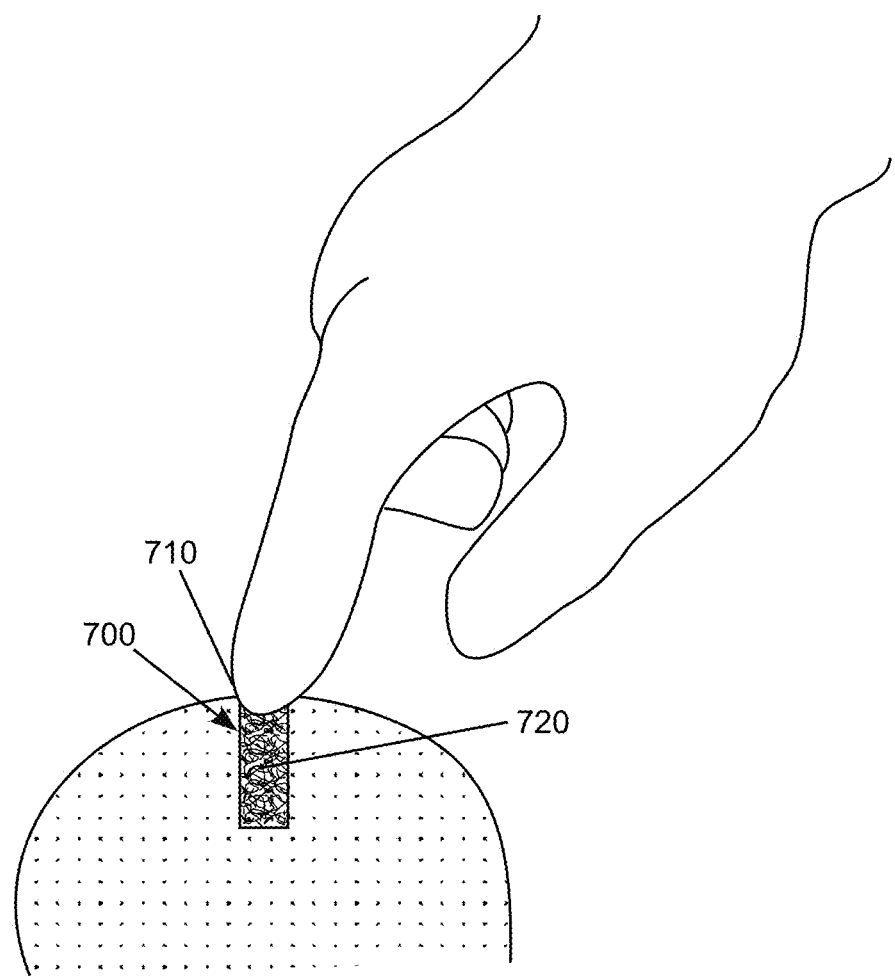
FIG. 4 depicts an insertion of an interlaced fibrous putty 720 into a confined tissue defect 700. The applied force 710 of the insertion is conducted by the interlaced fibers of the putty, forcing it into intimate contact with the walls defining the tissue defect.

Similarly, the interlocking of the interlaced fibers 110 retards dissolution of the device, allowing it to be used in confined wound spaces (e.g., a tissue void as shown in FIG. 4). FIG. 4 depicts an insertion of an interlaced fibrous putty 720 into a confined tissue defect 700. The applied force 710 of the insertion is conducted by the interlaced fibers of the putty, forcing it into intimate contact with the walls defining the tissue defect.

Figures 5A, 5B, 5C:
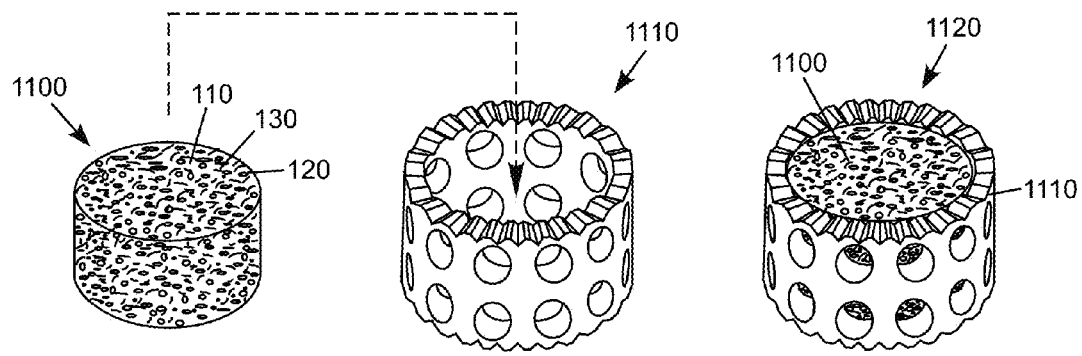
FIGS. 5A, B, and C depict a cylinder 1100 of interlaced fibers 110. The fibers are represented by open space defined by the dimensions of the cylinder. The interlocking of the interlaced fibers 110 supports, confines, and locks the particulate material 120 and biologically active agent 130 within a spatial conformation. The Cylinder 1100 is inserted inside of a preformed structure or cage 1110 creating a spinal implant 1120.
Figure 5D:
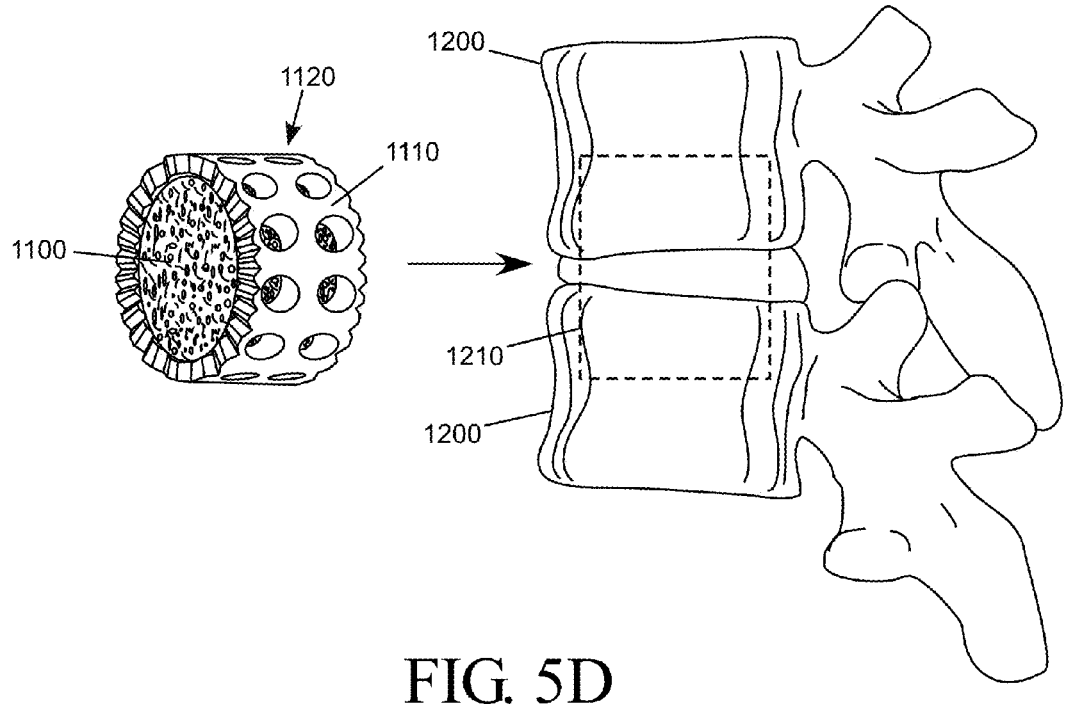
FIG. 5D depicts spinal implant 1120 being inserted into a defined space 1210 within two vertebral bodies 1200.

The presence of interlaced fibers 110 in the devices makes it particularly suited to those tissue defects exposed to irrigation, especially at volumes and/or flow rates where current state of the art putties fail (e.g., disintegrate, disassociate, break apart). The embodiment of FIG. 2 is suitable for, but not limited to: cell culture support and transfer, cartilage defect filling, bone void filling, soft tissue augmentation (e.g., removal of dermal creases) and periurethral bulking to combat urinary incontinences arising from such conditions as intrinsic sphincter deficiency. Additional possibilities include but are not limited to use as a spinal cage filler (as shown in FIG. 5), depicting a cylinder of interlaced fibers. The fibers are represented by open space defined by the dimensions of the cylinder. The interlocking of the interlaced fibers may support, confine, and lock the particulate material and biologically active agent within a spatial conformation (as will be discussed later). The cylinder 1100 of FIG. 5A, is inserted inside of a preformed structure 1110 of FIG. 5B, or cage creating a spinal implant 1120 of FIG. 5C, which may then be implanted substantially as shown in FIG. 5D.

Figure 8A:
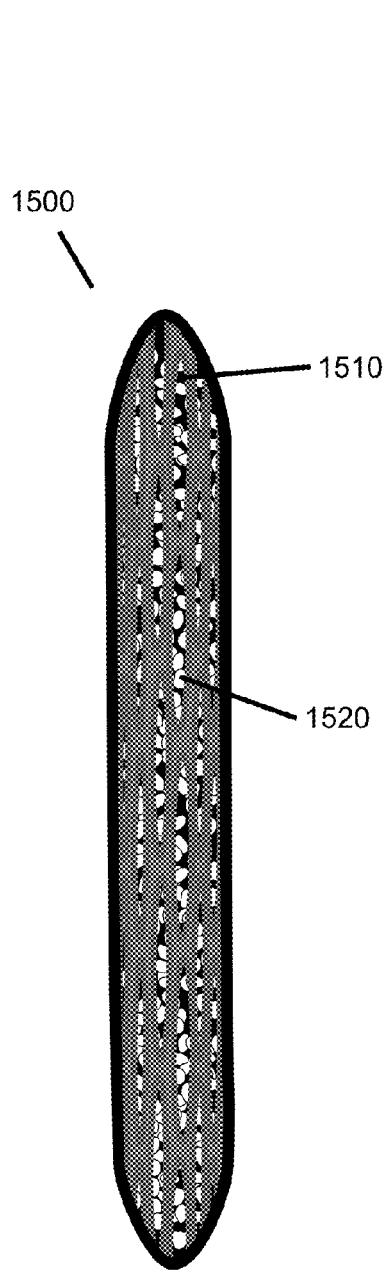
FIG. 8A depicts hollow intermedullary nail 1500 having openings 1510 containing graft material 1520 composed of interlaced, interlocked fibers and particulate.
Figure 8B:
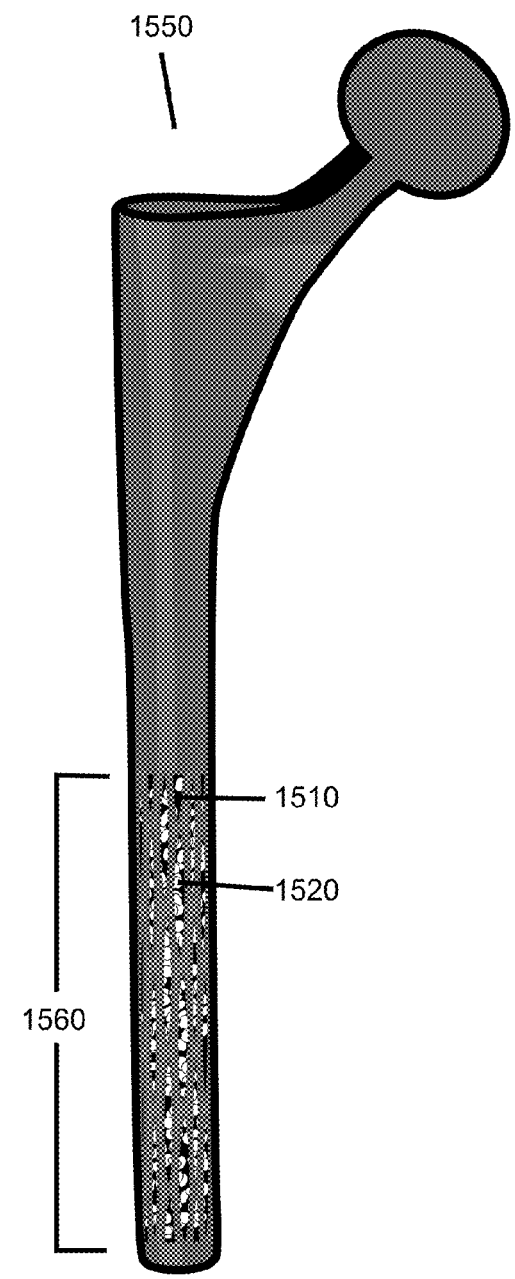
FIG. 8B depicts the femoral portion of artificial hip prosthesis 1550 having a hollow stem portion 1560 having openings 1510 containing graft material 1520 composed of interlaced, interlocked fibers and particulate.

An alternate use of the putty is depicted in FIGS. 8A and 8B, wherein the putty material is inserted inside of an intermedullary nail 1500 (FIG. 8A) and the femoral shaft portion 1560 of a hip prosthesis 1550 (FIG. 8B). At least a portion of the rigid implant, that which extends into the bone, would be porous, or hollow and containing holes 1510 through the wall of the implant capable of receiving the putty 1520 and allowing ingrowth of host tissue. This would allow bone to grow through and ultimately in and around the rigid implant, thereby effectively anchoring it to the rest of the surrounding bone. The putty utilized as a graft material may include particulates and/or biologically active agents. It is recognized that the particulate material itself may be functional as a biologically active agent (e.g. Demineralized Bone Matrix, etc.) The novel concept of providing a prosthesis containing a hollow zone(s) capable of receiving graft material is useful in the creation of dental implants or any other implant, which requires anchoring to host tissue such as an ocular prosthesis or mechanical heart valve.

Figure 6:
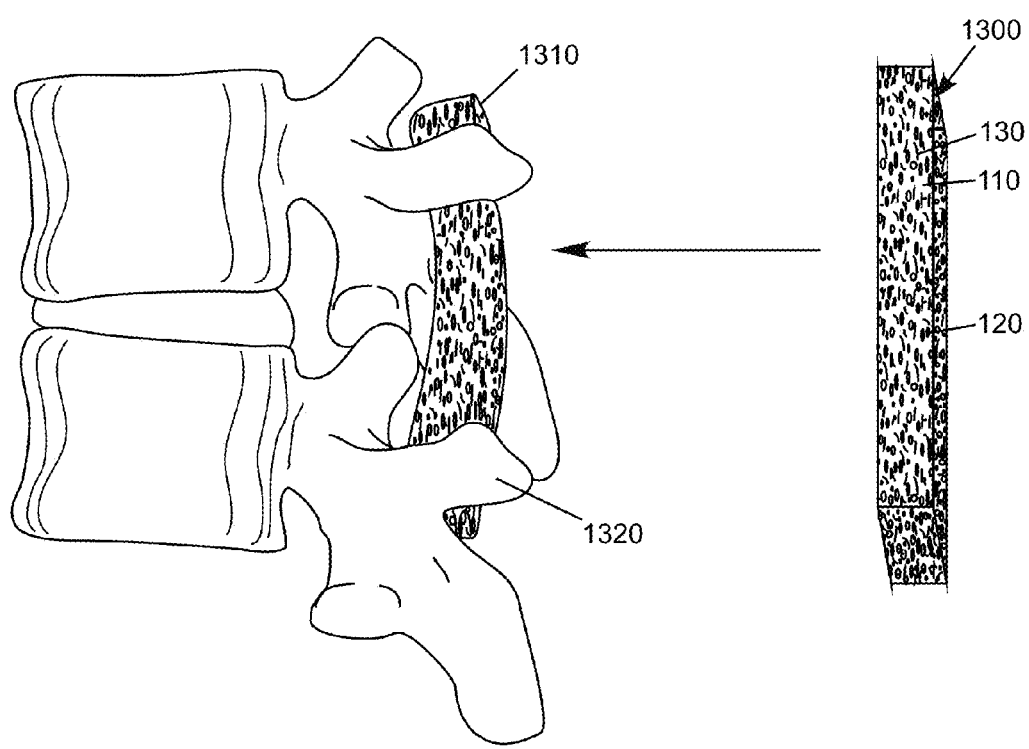
FIG. 6 depicts dry sheet 1300 of interlaced fibers 110. The fibers are represented by open space defined by the dimensions of the sheet. The interlocking of the interlaced fibers 110 supports, confines, and locks the particulate material 120 and biologically active agent 130 within a spatial conformation. As the dry sheet 1300 becomes hydrated, it becomes a conformable mass 1310 that can be approximated to the irregular topography of the transverse processes 1320 of the vertebrae.

Alternatively, FIG. 6 is another possible use for the putty, depicted as a graft overlay to retain osteoconductive/osteoinductive grafting material (e.g., harvested bone chip, ceramics, etc.) during a transverse process spinal fusion (as shown in FIG. 6). FIG. 6 depicts dry sheet 1300 of interlaced fibers 110. The fibers are represented by open space defined by the dimensions of the sheet. The interlocking of the interlaced fibers 110 may support, confine, and lock the particulate material 120 and biologically active agent 130 within a spatial conformation (as will be discussed later). As the dry sheet 1300 becomes hydrated, it becomes a conformable/malleable mass 1310 that can be approximated to the irregular topography of the transverse processes 1320 of the vertebrae. In these additional applications the malleable characteristics of the hydrated device will allow it to conform to the unique shaped chambers of the spinal cage or the irregular topography of the transverse process surgical site. In a transverse process surgical procedure the implant covers and secures the graft material (not shown) in place.

In another embodiment (not shown) the putty is preformed into a cup and utilized to retain graft material placed in and around the acetabulum during a hip reconstruction. The putty is then sandwiched between the host bone and the artificial cup that will receive the prosthesis. If additional toughness is required, the cup can be cross-linked to provide a flexible article that may further feature shape-memory. Additionally, the putty can be packed around the stem of the prosthesis prior to its insertion into the long bone channel. If desired, a novel prosthesis (as described above for FIGS. 8A and 8B) with a stem having a hollow cage-like appearance can be utilized. The putty is inserted into the cage wherein it is then dried and sterilized. Optionally, the dried putty can be cross-linked to prevent egress from the prosthesis. This same novel cage-like structure can be utilized for nails placed in the shaft of long-bones.

In another embodiment, the putty material contains reinforcing materials such as long threads, meshes or other fibers (not shown). The interlocking of the interlaced fibers supports, confines, and locks the reinforcing material within a spatial conformation. This retards the reinforcing material from migrating within or dissection from the putty or paste. This can be used to alter mechanical properties (e.g., compressive strength) as well as enhance resistance to disassociation of fibers form the construct. Additionally, the putty may improve the biocompatibility of the reinforcing material (e.g., improved cellular migration within or adhesion to a mesh). The reinforcing material may be centered within the construct, located on or just below one or more surfaces or interspersed throughout the entire construct.

In another embodiment the interlocking of the interlaced fibers is used to control the location and delivery of biologically active agents (e.g., growth factors, hormones, BMP, drugs, cells, viruses, etc.) (see table 2). The unique equiaxial formation of the device controls flow of fluid (e.g., blood, interstitial, etc.) within the device allowing for tailored release properties. The biologically active agents could be located within or supported between the fibers making up the device. Additionally, the biologically active agents could be mechanically or chemically attached or bonded to the fibers or suspended within a hydration fluid. This hydration fluid may contain a soluble polymer that suspends or binds the biologically active agent. Additionally, the hydration fluid containing the soluble polymer may be removed leaving the soluble polymer as a solid sheet or coating adhered to the fibers, an open laced network of strands adhered to the polymer fibers; a velour, felting or loosely woven sheet adhered to the polymer fibers; or as a porous foam or microstructure suspended between the fibers. In addition to supporting a biologically active agent, the hydrated soluble polymer can function as a lubricant to aid in partial de-interlacing of the polymer fibers during molding or implantation.

It is also conceived that in one embodiment of this invention the material can contain an additive that can be used to help deliver or retain the previously described biologically active agents. As an example, the interstices of the gross fibrous structure could be invested with a soluble polymer as defined above, e.g., a chemotactic ground substance, such as the velour of hyaluronic acid. A velour of chemotactic ground substance could accomplish several biochemical and biomechanical functions essential for wound repair. For example, since hyaluronic acid is extremely hydrophilic, it may be valuable for drawing body fluid (e.g., blood, bone marrow) or other fluid-based biologically active agents into the fibrous device. Upon hydration, the hyaluronic acid can become an ideal carrier for pharmacological or biologically active agents (e.g., osteoinductive or osteogenic agents such as the bone morphogenetic protein (BMP) and other bone-derived growth factors (BDGF)) by providing for chemical binding sites, as well as by providing for mechanical entrapment of the agent as the velour forms a hydrogel.

It is also conceived that a source of growth factors (e.g., platelet-rich plasma, bone marrow cells, etc.), whether synthetic, autologous or allograft in origination, can be delivered with the device of this invention (e.g., incorporated into the implant during manufacturing or integrated into the device prior to implantation). For example, it is known that one of the first growth factors to initiate the cascade leading to bone regeneration are platelet-derived growth factor (PDGF) and transforming growth factor-beta (TGF-β). Each of these growth factors is derived from the degranulation of platelets at the wound, defect or trauma site. It is believed that increasing the presence of such platelets at the wound or trauma site can increase the rate of healing and proliferation needed to regenerate tissue (e.g., bone).

The application of platelet-rich plasma (PRP) is one way to deliver a highly concentrated dose of autologous platelets. PRP is easily prepared by extracting a small amount of the patient's blood and processing it, for example, using gradient density centrifugation, to sequester and concentrate the patient's platelet derived growth factors. Other preparation methods remove water from the buffy coat (i.e., coagulated blood coating) and utilize filtering systems to concentrate platelets and fibrinogen. It is believed that applying PRP or other autologous growth factors to the wound site in conjunction with the subject invention will increase the amount of PDGF and TGF-β available for jump-starting the healing process. PRP can be prepared for procedures with small volumes of blood, drawn by the doctor or nurse presurgically. Typically, 40-100 ml of blood are drawn preoperatively and placed in a PRP preparation unit. SmartPREP (Harvest Technologies Corp., Norwell, Mass.) and Ultra-Concentrator (Interpore Cross, Irvine, Calif.) are devices that have been shown to effectively produce PRP for OR, office implant, and periodontal uses.

Once the PRP is prepared, other additives (e.g., activator, growth factor, drug, chemical, bone, etc.) can be added to the plasma. For example, to infuse the implant material of this invention with a PRP gel preparation, the ratio of ingredients would include a higher proportion of PRP to allow the PRP to more effectively flow through and permeate through the putty material. It is also conceived that the de-hydrated putty can be inserted into the PRP preparation unit (e.g., centrifuge, concentration unit). In this fashion, the platelets can be concentrated right into or onto at least a portion of the implant directly. For example, some PRP devices include a centrifuge for separation of the blood components. The biomaterial implant could be positioned within the centrifuge such that the desired blood constituent is directed into the implant material during processing.

Other autologous materials can also be incorporated into and used in conjunction with the subject invention (e.g., autologous bone marrow cells (BMC)). Bone marrow contains osteogenic progenitor cells that have the ability to form and repair bone. The marrow can be harvested and dispersed into single cell suspensions. The cells can then be concentrated (e.g., through filtering, centrifucation) or used as is. The resulting mixture can be diluted and implanted into the wound site, incorporated into the implant material, or delivered by the delivery system (e.g., syringe) with the materials of the subject invention.

In another embodiment, the interlocking of the interlaced fibers is used to control the location and orientation of particulate components compounded into the fibrous material (e.g., ceramic, glass, glass-ceramic, metals, tricalcium phosphate, Hydroxylapatite, calcium sulfate, autologous bone graft, allograft bone matrix, polymers, microspheres, microcapsules, hyaluronic acid, collagen, chitosan, alginate, poly-lactic acid, poly-glycolic acid, poly-caprolactone, polyurethane, etc). The particulate components may additionally carry or serve to deliver biologically active agents. The interlacing supports, confines, and locks the particulate components within a spatial conformation. This retards the particulate from migrating within or disassociating from the putty or paste. (When the fibrous material is combined with a fine powdered ceramic, the consistency is more chalk-like than that of putty or paste formed with larger ceramic particulate.) A fibrous slurry containing particulate may be concentrated using centrifugation as mentioned above, or particulate may be added as a solute to a rehydrating solvent. Alternatively, the particulate may be mechanically incorporated (e.g., kneaded) into the interlaced fibrous putty. The resulting material may be implanted or dried and rehydrated with a volume of liquid to yield a desired density or consistency to the paste or putty. It should be noted that previously dried putty is suitable for implantation dry wherein it is rehydrated by body fluids (e.g., blood).

When adding particulate, the addition of a soluble polymer to increase the viscosity of the aqueous solution prevents premature separation or stratification of the particulate from the collagen fibers in the final product. Additionally, the fluid containing the soluble polymer can be removed, leaving the particulate entrapped within the soluble polymer as a coating on the fibers or suspended between the fibers.

When porous particulates are used, the fibers randomly penetrate the pores and become interlaced along with the fibers, creating a single continuous network of fibers and particulate. The particulate may create a type of hub with fibers radiating out to other hubs. This creates a unique structure wherein particulate loss is reduced. Additionally, cells migrating into the structure along the fibers may be guided to the incorporated particulate.

The concentrations of the putty or paste, as well as the extent of interlacing between fibers that result from centrifuging, produce characteristics that range from smooth injectable gels to highly compact masses with elastic type qualities. For instance, the centrifuge may be used to spin down fibrous slurry into blocks or uniquely shaped molds (e.g., tubes, ears, nose, cones, brick, plate, disk, ellipse, sheet, membrane, wedge, pin, rod, cylinder, roles, cup, sphere, semi-sphere, pyramid and a frustum of a cone, wedge or pyramid, etc). Additionally, material properties provided by the action of partial de-interlacing (as described previously) of centrifuged fibrous slurry allow the material to be: 1) injected through a syringe; 2) pressed between plates; 3) injection molded; 4) rolled out into flat sheets; 5) carved and/or formed like clay; or 6) aerated. This partial de-interlacing allows for an additional way in which to form shapes listed above.

In an embodiment, there may be a benefit to the creation of an interlaced and interlocked fibrous composition as described above, further featuring a plurality of pores. The pores may be created by techniques known in the art (e.g., a gas expansion process, a freeze drying process, etc.). The pores may be of a closed cell morphology, open cell and intercommunicating morphology, or a combination of both. The pores may be of a regular, ordered size or shape, or alternatively may vary in size or shape. The shape and size of the pore may be manipulated through various pore formation techniques known in the art.

For example, the flow caused by the movement of the fibers during centrifuging may create equiaxial and/or elongated pores (dependant of fiber length) within the final product post-drying (e.g., lyophilization, air-dried, etc.) Additionally, freeze rate, freeze direction, temperature gradients and insolubles (fibers and particulate) can be used to control crystal formation, that in turn controls pore size, shape and orientation. Furthermore, as the liquid freezes to solid crystals, the fibers and particulates have an impact on pore formation as they potentially interfere with crystal growth. As the temperature of a mixture is lowered, crystals form within the fluid surrounding the fibers and particulate. As the crystals grow they force the fiber and particulate material aside, thereby effectively increasing the concentration of the material between the crystals. The growth of the crystals may be disrupted as they come in contact with the fibers and particulate. This interruption of crystal growth, either stops the growth of the crystal or forces them to grow around the particles in an irregular fashion. After solidification the crystals of the frozen liquid are removed by methods know in the art (e.g. vacuum drying or leaching) leaving irregular pores.

Figure 7:
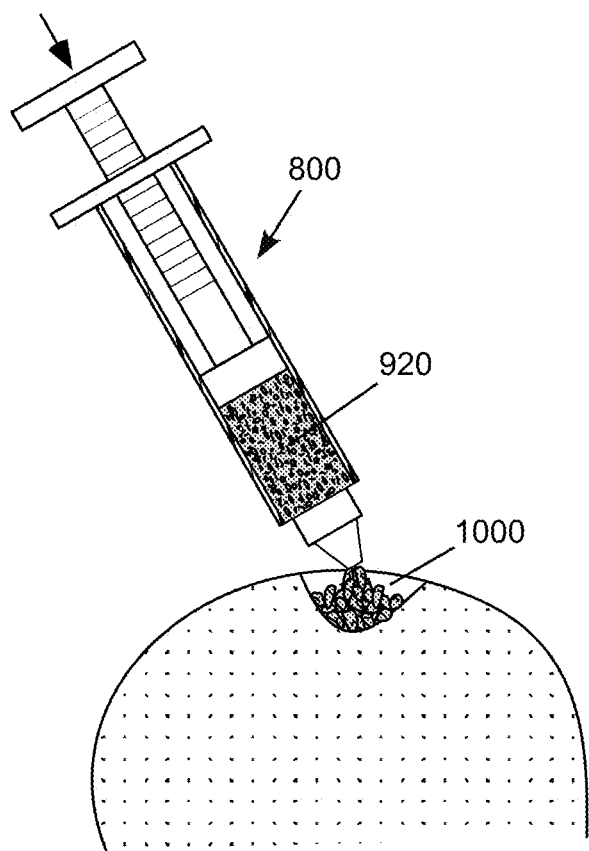
FIG. 7 depicts the injection of a hydrated malleable mass 920 of interlaced fibers from a syringe 800 into a tissue defect 1000.

Orientation of fibers, along with the interlacing (to keep the fibers as one mass), that allows putty-like dispersions to be injected through a syringe. This is depicted in FIG. 7, wherein the syringe 800 injects a hydrated malleable mass 920 of interlaced fibers into a tissue defect 1000. The capability of the fibrous implant material in the form of the hydrated malleable mass 920 to be delivered via syringe 800 makes it suitable for use in laparoscopic, arthroscopic and endoscopic procedures. These minimally invasive surgical procedures utilize cannulas and trocars to remotely treat or repair a variety of injuries or maladies. It should be understood that the fibrous implant's unique viscosity allow for the delivery of the material to remote sites within the body. Once delivered, the material can remain intact and stable at the delivery location for a period of time post implantation.

It should also be noted that use of reinforcing materials (polymer mesh, tricalcium phosphate, etc.) or addition of biologically active agents (growth factors, DBM, cells, drugs, etc.) may be employed as a particulate or other addition. Additions may be made in an effort to increase the viscosity of the pre-centrifuge process liquid, but the addition may also be used to coat the fibers. This fiber coating may be employed to tailor the inner environment of the material, and may improve, e.g., the osteoconductivity or osteoinductivity. These coatings or other additions may be uniformly dispersed throughout the fibrous structure, or more sporadic. In a preferred embodiment, the coating or additive will create a microstructure, adherent to the fibrous macrostructure. In certain embodiments with microstructural additions the microstructure may be more prominent at junction points, or regions where several fibers come in contact with each other. In a preferred embodiment these microstructurally coated junctions serve to attract and nourish the inbound cells.

In another embodiment, the centrifuge process yields a material with a viscous high-density structure that, in itself, is useful for surgical procedures. For example, this unique fiber arrangement, regardless of the degree of interlacing or interlocking, if any, renders the material suitable for hand molding or injecting via syringe. The unique three-dimensional nature of this structure of this material exhibits properties not seen in the art.

In another embodiment, the materials made by these various processes may be cross-linked to impart improved characteristics such as: mechanical strength (e.g., suturablity, compression, tension, etc.), and biodurability (e.g., resistant to enzymatic and hydrolytic degradation). This may be accomplished using several different cross-linking agents, or techniques (e.g., thermal dehydration, EDC, aldehydes (e.g., formaldehyde, gluteraldehyde, etc.), natural cross-linking agents such as genipin or proanthocyanidin, and combinations thereof). Each type of cross-linking agent/technique or combinations thereof imparts diverse mechanical and biological properties on the material. These properties are created through the formation of unique chemical bonds that stabilize the construct. This stabilization greatly increases the construct's ability to hold a shape and conformation, thereby, preserving the interlaced relationship between the fibers.

As an example of cross-linking, the construct may be placed in 100 mM EDC solution contained in pH 5.4 MES buffer for 1 minute to 24 hours, preferably 4 hours. This creates a chemical bond between amino and carboxyl acid groups to form amide linkages. The device is then rinsed and dried by either lyophilization or simple evaporation.

This newly stabilized device, containing interlaced fibers, has superior mechanical and biological properties as compared to prior art constructs. The interlaced fibrous structure guides cellular ingrowth creating newly regenerated tissue that more closely approximates natural tissue than can be achieved via a random structure. Additionally, the three dimensional interlaced structure allows for the occurrence of directional, biomechanical stimulus useful in the regeneration of tissue which is exposed to mechanical motion. This can be seen in tissues such as cartilage, intervertebral discs, joint meniscus, blood vessel, heart valves, or the like.

In various embodiments of the invention the collagen putty, that has been formed or shaped by any methods known to those skilled in the art, can be cross-linked to create uniquely shaped biodurable medical devices (not shown). The devices may take on forms such as sheets, tubes, roles, blocks, cylinders brick, plate, disk, ellipse, membrane, wedge, pin, rod cup, sphere, semi-sphere, cone, pyramid, frustum of a cone, wedge or pyramid or pads useful for tissue augmentation, replacement, or repair. Additionally the devices can be shaped into unique anatomically specific shapes (e.g. nose, ear, chin, etc).

In one embodiment the interlocking of the interlaced fibers allows a highly concentrated putty to be rolled flat and stressed in three dimensions simultaneously, producing an intact sheet that can be cross-linked; whereas directionally oriented fibers would tear apart or experience separation during the flattening process (not shown). Therefore, this material would be useful in such applications as, but not limited to dura repair, skin grafting procedures, hernia repair, rotator cuff repair, ligament repair or bladder support or repair.

In another embodiment (not shown) the sheet produced in the previous embodiment is rolled prior to cross-linking to create a unique spiral configuration having a plane separating each successive revolution of the sheet. The plane provides unique compressive qualities, that when combined with the compressive qualities of the cross-linked interlaced fibers, is ideal for applications receiving directional compressive loads. These applications include but are not limited to joint meniscus, intervertebral disk and articular cartilage.

In another embodiment the plane formed by the spiral configuration can be filled with materials to enhance its mechanical or biologic characteristics (e.g., reinforcing materials, particulates, biologically active agents, natural and synthetic polymers).

Various of these shaped embodiments may also be manufactured in composite laminate form. That is, flat sheet or shaped embodiments, may be affixed to other materials, by pressing, gluing, or means known to those skilled in the art. These macro-composites may combine the materials of these embodiments with material, i.e., with higher strength, osteo conductivity, resorbability, etc.

In another embodiment (not shown) a fibrous collagen slurry can be spun down into a mold that approximates the gross anatomy of a tissue or organ (e.g., blood vessel, heart valve, ear, nose, breast, finger-bones, long bone, acetabular cup, etc.) prior to cross-linking. The interlocking of the interlaced fibers, formed during this process, provides superior shape holding characteristics due to the unique resistance to fiber disassociation, as previously described. Constructs made using oriented fibers defined in prior art do not hold crisp margins. Therefore, material in this embodiment would be useful as, but not limited to, devices for cosmetic and reconstructive surgery, intervertebral disks, joint meniscus and hollow tissues and organs (e.g., intestine, esophagus, ureter, etc.).

In another embodiment (not shown) a fibrous collagen slurry can be spun down into a mold containing a structure or component (e.g., ring, mesh, particulate, screw, rod, screen, etc.) to which the interlaced fibers migrate around, thereby creating a mechanical lock, after which cross-linking may occur. The interlocking of the interlaced fibers supports, confines, and locks the structure or component within a spatial conformation.

In another embodiment (not shown) the partial de-interlacing of zones within a putty or paste facilitates compression or injection of the material into or around structures such as, but not limited to: molds, screws, rings, rods, cavities, meshes or screens. Injected into a tube mold the material would be suitable as a vascular graft or nerve conduit. Injected into more massive and possibly complex shapes, the material would be suitable for applications such as: intervertebral disks, soft tissue augmentation, ocular prosthesis, joint meniscus, bone void or soft tissue filler, and applications in plastic and reconstructive surgery.

Additionally, material may contain reinforcing materials such as long polymer threads or meshes or may include particulates or biologically active agents. (e.g., growth factors, hormones, bmp, drugs, cells, viruses, etc.) Additionally, the biologically active agents could be located within fibers making up the putty, mechanically or chemically attached to the fibers making up the putty, between the fibers, or suspended within a hydration fluid or second soluble polymer intermixed with the fibers of the putty material. The biologically active agents and/or soluble polymer intermixed with the fiber may be added prior to or after cross-linking.

It is conceived the interlaced polymer material may be manufactured by the centrifugation process heretofore described, and may be sterilized and packaged, or alternatively dried (e.g., by lyophilization or evaporative processes) then sterilized and packaged for later use. It is also recognized that either the wet product or the dry product may be terminally sterilized.

The following examples are given for purposes of illustration to aid in understanding the invention and it is to be understood that the invention is not restricted to the particular conditions, proportions and reagents set forth therein.

Example 1

Fibrous Collagen, 4% solids in water by weight, pH 5.3-5.9, was placed mixed with powdered (6 micrometers) β-tricalcium phosphate until a homogeneous mixture was achieved. This dispersion was centrifuged at 3200×g for 2 minutes to reduce the mixture 40% by volume. The supernatant was poured off and discarded. The "pellet" was removed from the centrifuge tube, placed in a mold, and freeze-dried. This same processed was followed with a larger particle size (500-1000 micrometers) β-tricalcium phosphate. When centrifuged under the same conditions the resulting dispersion was reduced 60% by volume.

Example 2

Fibrous Collagen, 4% solids in water by weight, pH 5.3-5.9, was placed in a centrifuge tube. The dispersion was centrifuged at 8000×g for 24 hours. The supernatant was poured off. The solution was reduced by ~90% volume loss. This dough-like mass was then shaped into a mold and freeze-dried. The resultant sponge was then cross-linked using a thermal dehydration to lock in the molded shape. Upon rehydration, the resultant sponge held its shape and showed high resistance to compression. It was also noted that the sponge contained some elastic properties. These elastic properties allowed the sponge to be warped, twisted, and manipulated after which it returned to its original confirmation, thereby displaying shape memory. This may be useful when inserting through a narrowing.

Example 3

Fibrous Collagen, 4% solids in water by weight, pH 5.3-5.9, was placed in a centrifuge tube. The dispersion was centrifuged at 8000×g for 4-5 hours. The supernatant was poured off. The solution was reduced by ~80% volume loss. This dough-like mass was then rolled flat using a rolling pin or a two roller system to create a high fiber density sheet. The sheet was freeze-dried and cross-linked using a 100 mM EDC solution (pH 5.4) in water. The sheet was allowed to soak in the cross-linking solution overnight and then serially rinsed 3× for 2 hours with agitation in water. This sheet exhibited high resistance to tearing and ripping.

TABLE 1

| Examples of Biodegradable Polymers for Construction of the Device |
| --- |
| Aliphatic polyesters |
| Bioglass |
| Cellulose |
| Chitin |
| Collagen |
| Copolymers of glycolide |
| Copolymers of lactide |
| Elastin |
| Fibrin |
| Glycolide/l-lactide copolymers (PGA/PLLA) |
| Glycolide/trimethylene carbonate copolymers (PGA/TMC) |
| Hydrogel |
| Lactide/tetramethylglycolide copolymers |
| Lactide/trimethylene carbonate copolymers |
| Lactide/ϵ-caprolactone copolymers |
| Lactide/σ-valerolactone copolymers |
| L-lactide/dl-lactide copolymers |
| Methyl methacrylate-N-vinyl pyrrolidone copolymers |
| Modified proteins |
| Nylon-2 |
| PHBA/γ-hydroxyvalerate copolymers (PHBA/HVA) |

TABLE 1-continued

Examples of Biodegradable Polymers
for Construction of the Device

PLA/polyethylene oxide copolymers
PLA-polyethylene oxide (PELA)
Poly (amino acids)
Poly (trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyglycolide (PGA)
Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-β- hydroxypropionate (PHPA)
Poly-β-hydroxybutyrate (PBA)
Poly-σ-valerolactone
Poly-β-alkanoic acids
Poly-β-malic acid (PMLA)
Poly-ε-caprolactone (PCL)
Pseudo-Poly(Amino Acids)
Starch
Trimethylene carbonate (TMC)
Tyrosine based polymers

TABLE 2

Examples of Biological, Pharmaceutical, and other Therapies
or Agents Deliverable via the Present Invention Adenovirus with or without genetic material
Alcohol
Amino Acids
    L-Arginine
Angiogenic agents
Angiotensin Converting Enzyme Inhibitors (ACE inhibitors)
Angiotensin II antagonists
Anti-angiogenic agents
Antiarrhythmics
Anti-bacterial agents
Antibiotics
    Erythromycin
    Penicillin
Anti-coagulants
    Heparin
Anti-growth factors
Anti-inflammatory agents
    Dexamethasone
    Aspirin
    Hydrocortisone
Antioxidants
Anti-platelet agents
    Forskolin
    GP IIb-IIIa inhibitors
    eptifibatide
Anti-proliferation agents
    Rho Kinase Inhibitors
    (+)-trans-4-(1-aminoethyl)-1-(4-pyridylcarbamoyl)
    cyclohexane

TABLE 2-continued

Examples of Biological, Pharmaceutical, and other Therapies
or Agents Deliverable via the Present Invention Anti-rejection agents
    Rapamycin
Anti-restenosis agents
    Adenosine $A_{2A}$ receptor agonists
Antisense
Antispasm agents
    Lidocaine
    Nitroglycerin
    Nicarpidine
Anti-thrombogenic agents
    Argatroban
    Hirudin
    GP IIb/IIIa inhibitors
Anti-viral drugs
Arteriogenesis agents
    acidic fibroblast growth factor (aFGF)
    angiogenin
    angiotropin
    basic fibroblast growth factor (bFGF)
    Bone morphogenic proteins (BMP)
    epidermal growth factor (EGF)
    fibrin
    granulocyte-macrophage colony stimulating factor (GM-CSF)
    hepatocyte growth factor (HGF)
    HIF-1
    insulin growth factor-1 (IGF-1)
    interleukin-8 (IL-8)
    MAC-1
    nicotinamide
    platelet-derived endothelial cell growth factor (PD-ECGF)
    platelet-derived growth factor (PDGF)
    transforming growth factors alpha & beta (TGF-.alpha., TGF-beta.)
    tumor necrosis factor alpha (TNF-.alpha.)
    vascular endothelial growth factor (VEGF)
    vascular permeability factor (VPF)
Bacteria
Beta blocker
Blood clotting factor
Bone morphogenic proteins (BMP)
Calcium channel blockers
Carcinogens
Cells
Chemotherapeutic agents
    Ceramide
    Taxol
    Cisplatin
Cholesterol reducers
Chondroitin
Collagen Inhibitors
Colony stimulating factors
Coumadin
Cytokines prostaglandins
Dentin
Etretinate
Genetic material
Glucosamine
Glycosaminoglycans
GP IIb/IIIa inhibitors
    L-703,081
Granulocyte-macrophage colony stimulating factor (GM-CSF)
Growth factor antagonists or inhibitors
Growth factors
    Bone morphogenic proteins (BMPs)
    Core binding factor A
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived Growth Factor (PDGF)
    Recombinant NGF (rhNGF)
    Tissue necrosis factor (TNF)
    Transforming growth factors alpha (TGF-alpha)
    Transforming growth factors beta (TGF-beta)
    Vascular Endothelial Growth Factor (VEGF)
    Vascular permeability factor (UPF)

TABLE 2-continued

Examples of Biological, Pharmaceutical, and other Therapies
or Agents Deliverable via the Present Invention Acidic fibroblast growth factor (aFGF)
Basic fibroblast growth factor (bFGF)
Epidermal growth factor (EGF)
Hepatocyte growth factor (HGF)
Insulin growth factor-1 (IGF-1)
Platelet-derived endothelial cell growth factor (PD-ECGF)
Tumor necrosis factor alpha (TNF-.alpha.)
Growth hormones
Heparin sulfate proteoglycan
HMC-CoA reductase inhibitors (statins)
Hormones
    Erythropoietin
Immoxidal
Immunosuppressant agents
inflammatory mediator
Insulin
Interleukins
Interlukin-8 (IL-8)
Interlukins
Lipid lowering agents
Lipo-proteins
Low-molecular weight heparin
Lymphocites
Lysine
MAC-1
Methylation inhibitors
Morphogens
Nitric oxide (NO)
Nucleotides
Peptides
Polyphenol
PR39
Proteins
Prostaglandins
Proteoglycans
    Perlecan
Radioactive materials
    Iodine - 125
    Iodine - 131
    Iridium - 192
    Palladium 103
Radio-pharmaceuticals
Secondary Messengers
    Ceramide
Somatomedins
Statins
Stem Cells
Steroids
Surfactants
    tween
    triton
    polysorbate
    witconate
    sulfonic tea
    sodium oleate
Thrombin
Thrombin inhibitor
Thrombolytics
Ticlid
Tyrosine kinase Inhibitors
    ST638
    AG-17
Vasodilators
    Histamine
    Forskolin
    Nitroglycerin
Vitamins
    E
    C
Yeast
Ziyphi fructus The inclusion of groups and subgroups in Table 2 is exemplary and for convenience only. The grouping does not indicate a preferred use or limitation on use of any drug therein. That is, the groupings are for reference only and not meant to be limiting in any way (e.g., it is recognized that the Taxol formulations are used for chemotherapeutic applications as well as for anti-restenotic coatings). Additionally, the table is not exhaustive, as many other drugs and drug groups are contemplated for use in the current embodiments. There are naturally occurring and synthesized forms of many therapies, both existing and under development, and the table is meant to include both forms.

What is claimed is:

1. A method of creating a malleable, biocompatible polymer material for the repair or replacement of tissue, comprising the steps of:
   a. providing a vessel containing a slurry, said slurry comprising a plurality of polymer fibers and at least one suspension fluid, wherein said slurry has a percentage mass of polymer fibers dispersed in the suspension fluid of less than about 10% by weight and wherein the polymer fibers are substantially evenly dispersed and randomly oriented throughout the volume of the suspension fluid;
   b. applying a centrifugal force to said vessel containing said slurry, in such a way that said centrifugal force serves to cause said polymer fibers to migrate through the suspension fluid and amass at a furthest extent of the vessel, forming a polymer material, with said polymer material comprising polymer fibers of sufficient length and sufficiently interlaced and interlocked to retard dissociation of said polymer fibers upon contact with a fluid, thereby forming a polymer putty;
   c. removing said polymer putty from said vessel and from said suspension fluid;
   d. shape forming said polymer putty into a defined cup shape; and
   e. extracting said suspension fluid from said polymer implant to form a dried polymer material.

2. The method of claim 1, further comprising the step of:
f. sterilizing said dried polymer material.

3. The method of claim 2, further comprising the step of:
g. adding a rehydrating fluid to the dried cup shaped polymer material to restore malleability.

4. The method of claim 3, wherein said rehydrating fluid comprises a biologically active agent.

5. The method of claim 4, wherein said biologically active agent comprises at least one of blood, platelet rich plasma, bone marrow cells, stem cells, growth factors, autograft and allograft.

6. The method of claim 3, wherein said rehydrating fluid is integrated into the dried polymer material prior to implant.

7. The method of claim 1, wherein said slurry has a percentage mass of polymer fibers dispersed in the suspension fluid in the range of about 3 to about 5% by weight.

8. The method of claim 1, wherein at least a portion of said polymer is at least one of collagen, chitosan, alginate, hyaluronic acid, poly-lactic acid, poly-glycolic acid, poly-caprolactone, and polyurethane.

9. The method of claim 1, wherein said slurry further comprises a biocompatible particulate.

10. The method of claim 9, wherein said particulate is at least one of calcium phosphate ceramics, glass, glass-ceramic, metals, autologous bone graft, allograft bone matrix, hyaluronic acid, hydroxyapatite, collagen, chitosan, alginate, hyaluronic acid, microspheres, microcapsules poly-lactic acid, poly-glycolic acid, poly-caprolactone, and polyurethane.

11. A biocompatible composition comprising a network of randomly interlaced and interlocked polymer fibers in the form of a defined cup shape, said biocompatible composition being suitable for implantation into a living being, and wherein said network resists dissociation of said polymer fibers when contacted with a fluid.

12. The composition of claim 11, wherein at least a portion of said polymer is at least one of collagen, chitosan, alginate, hyaluronic acid, poly-lactic acid, poly-glycolic acid, poly-caprolactone, and polyurethane.

13. The composition of claim 12, further comprising a biocompatible particulate.

14. The method of claim 1, wherein said slurry further comprises a lubricant.

15. The composition of claim 11, wherein said composition further comprises at least one of blood, platelet rich plasma, bone marrow cells, stem cells, growth factors, autograft and allograft.

16. The composition of claim 13, wherein said biocompatible particulate comprises a plurality of pores.

17. The composition of claim 16, wherein said fibers are arranged in such a manner so as to be at least partially interlaced within said pores of the biocompatible particulate.

18. The composition of claim 13, wherein said particulate is at least one of calcium phosphate ceramics, glass, glass-ceramic, metals, autologous bone graft, allograft bone matrix, hyaluronic acid, hydroxyapatite, collagen, chitosan, alginate, hyaluronic acid, microspheres, microcapsules poly-lactic acid, poly-glycolic acid, poly-caprolactone, and polyurethane.

19. The composition of claim 11, further comprising a second polymer, said second polymer being soluble, and wherein said polymer fibers are surrounded by said second soluble polymer.

20. The composition of claim 19, wherein said second soluble polymer is arranged to provide lubrication for said fibers, whereupon said composition becomes at least partially de-interlaced and shapeable.

21. The composition of claim 19, wherein said second soluble polymer further comprises a biologically active agent.

22. The composition of claim 11, wherein said polymer fibers are at least partially de-interlaced, whereupon said composition becomes shapeable.

23. A method of creating a malleable, biocompatible polymer material for the repair or replacement of tissue, comprising the steps of:
   a. providing a vessel containing a low concentration slurry, said slurry comprising a plurality of polymer fibers and at least one suspension fluid, wherein the polymer fibers are substantially evenly dispersed and randomly oriented throughout the volume of the suspension fluid;
   b. applying a gyroscopic force to said vessel containing said slurry, whereupon said gyroscopic force serves to cause said polymer fibers to flocculate and migrate through the suspension fluid and amass at a center point of the vessel, forming interlaced, flocculated fibers;
   c. exposing said interlaced, flocculated fibers to a force that extracts at least a portion of said suspension fluid, thereby allowing the interlaced, flocculated fibers to become interlocked with one another;
   d. removing said polymer material from said vessel and from said suspension fluid;
   e. shape forming said polymer material of step d, to form a defined cup shape; and
   f. lyophilizing said cup shaped polymer material of step e, to form a dried polymer material.

24. The method of claim 23, further comprising the step of: g. sterilizing said dried polymer material.

25. The method of claim 24, further comprising the step of: g. adding a rehydrating fluid to the dried polymer material to restore malleability.

26. The method of claim 25, wherein said rehydrating fluid comprises a material selected from the group consisting of blood, platelet rich plasma, bone marrow cells, stem cells, growth factors, autograft and allograft.

27. The method of claim 25, wherein said rehydrating fluid is integrated into the dried polymer material prior to implant.

28. The method of claim 23, wherein said slurry has a percentage mass of polymer fibers dispersed in the suspension fluid of less than about 15% by weight.

29. The method of claim 23, wherein said slurry further comprises a biocompatible particulate.

30. The method of claim 29, wherein said particulate is at least one of calcium phosphate ceramics, glass, glass-ceramic, metals, autologous bone graft, allograft bone matrix, hyaluronic acid, hydroxyapatite, collagen, chitosan, alginate, hyaluronic acid, microspheres, microcapsules poly-lactic acid, poly-glycolic acid, poly-caprolactone, and polyurethane.

* * * * *